United States Patent

Matthews et al.

[11] Patent Number: 5,984,969
[45] Date of Patent: *Nov. 16, 1999

[54] JOINT PROSTHESIS AUGMENTATION SYSTEM

[75] Inventors: Frank D. Matthews, Walpole; Robert S. Brown, Boston; Gerald J. Cicierega, Bridgewater; Robert Hurlburt, Whitman; Michael J. O'Neil, West Barnstable, all of Mass.

[73] Assignee: Johnson & Johnson Professional, Inc., Raynham, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/563,775

[22] Filed: Nov. 28, 1995

Related U.S. Application Data

[63] Continuation-in-part of application No. 08/456,476, Jun. 1, 1995, abandoned.

[51] Int. Cl.[6] .................................................. A61F 2/38
[52] U.S. Cl. .............................................. 623/20; 623/18
[58] Field of Search ...................... 623/20, 18; 24/573.2, 24/588, 297; 411/508, 913; 606/72, 73, 62, 63, 65

[56] References Cited

U.S. PATENT DOCUMENTS

| | | | |
|---|---|---|---|
| 1,664,566 | 4/1928 | Marshall | 411/913 |
| 1,816,970 | 3/1931 | Hess | 411/508 |
| 2,490,364 | 2/1949 | Livingston | 128/92 |
| 3,076,453 | 2/1963 | Tronzo | 128/92 |
| 4,312,614 | 1/1982 | Palmer et al. | 411/508 |
| 4,711,232 | 12/1987 | Fischer et al. | 128/92 YF |
| 4,769,039 | 9/1988 | Horber | 623/20 |
| 4,778,473 | 10/1988 | Matthews et al. | 623/20 |
| 4,878,791 | 11/1989 | Kurihara et al. | 411/55 |
| 4,936,847 | 6/1990 | Manginelli | 623/16 |
| 4,936,853 | 6/1990 | Fabian et al. | 623/20 |
| 4,950,298 | 8/1990 | Gustilo et al. | 623/20 |
| 4,952,106 | 8/1990 | Kubogochi et al. | 411/508 |
| 4,995,883 | 2/1991 | Demane et al. | 623/23 |
| 5,039,267 | 8/1991 | Wollar | 411/508 |
| 5,080,674 | 1/1992 | Jacobs et al. | 623/20 |
| 5,108,446 | 4/1992 | Wagner et al. | 623/22 |
| 5,152,796 | 10/1992 | Slamin | 623/20 |
| 5,201,769 | 4/1993 | Schutzer | 623/23 |
| 5,222,984 | 6/1993 | Forte | 623/22 |
| 5,226,915 | 7/1993 | Bertin | 623/20 |
| 5,268,001 | 12/1993 | Nicholson et al. | 606/72 |
| 5,344,461 | 9/1994 | Phlipot | 623/20 |
| 5,387,241 | 2/1995 | Hayes | 623/20 |
| 5,429,467 | 7/1995 | Gugle et al. | 411/508 |
| 5,549,685 | 8/1996 | Hayes | 623/20 |

FOREIGN PATENT DOCUMENTS

| | | |
|---|---|---|
| 0433121 | 6/1991 | European Pat. Off. . |
| 0634154 | 1/1995 | European Pat. Off. . |
| 3930033 | 3/1990 | Germany . |
| 2223174 | 4/1990 | United Kingdom . |
| 2266246 | 10/1993 | United Kingdom . |

*Primary Examiner*—John G. Weiss
*Assistant Examiner*—Bruce E. Snow
*Attorney, Agent, or Firm*—Nutter, McClennen & Fish, LLP

[57] ABSTRACT

An augmentation system for an implantable bone prosthesis, such as a femoral component of a knee joint prosthesis, includes an augmenting block having an aperture disposed therein. A collet having an expandable distal end, extending beyond one surface of the augmenting block, is positioned within the aperture. The proximal end of the collet includes a cavity that receives an expansion pin that is adapted to communicate with the collet to expand the collet. The distal end of the collet is adapted to fit within a mounting cavity of a joint prosthesis. With the augmenting block placed on the appropriate surface of the joint prosthesis, the distal end of the collet is positioned within the mounting cavity. Advancement of the expansion pin causes the distal end of the collet to expand, thus frictionally and/or mechanically engaging the interior walls of the mounting cavity to firmly secure the augmenting system to the prosthesis. The expansion pin can include threads which mate with corresponding threads within the cavity of the collet. Alternatively, the pin and collet cavity can include ratchet and pawl-like surface features.

33 Claims, 9 Drawing Sheets

JOINT PROSTHESIS AUGMENTATION SYSTEM

This is a continuation-in-part of U.S. patent application Ser. No. 08/456,476, filed Jun. 1, 1995, now abandoned.

BACKGROUND OF THE INVENTION

This invention relates to devices useful to augment bone deficiencies encountered during joint arthroplasty procedures.

Joint arthroplasty is a well known surgical procedure by which a diseased and/or natural joint is replaced by a prosthetic joint. Joint arthroplasty is commonly performed for knees, hips, elbows, and other joints. In some instances, due to disease or trauma, insufficient healthy boney mass exists at the distal end of a bone to which a joint prosthesis is to be secured. In arthroplasty procedures, it is often necessary to remove a portion of bone (such as a portion of the femur) to ensure sufficient anchoring and a proper fit for a prosthesis. In the example of knee joint arthroplasty, it is sometimes necessary to augment the inferior portion of the femoral component of the prosthesis to add additional thickness to the prosthesis to compensate for the lack of sufficient boney tissue.

Augmentation of the boney mass can be accomplished by securing augmenting devices to a component of the joint prosthesis, such as a femoral component. Some earlier devices used to augment knee femoral components must be cemented to the inferior surface of the femoral component. The techniques used to install such devices require accurate measurements and a great deal of precision since the augmenting device is difficult, if not impossible, to remove once it is secured to the prosthesis. These techniques also tend to be rather time consuming.

An improved augmentation device is described in U.S. Pat. No. 4,936,847 (Manginelli). This patent discloses an augmentation system that can be removeably and replaceably secured within a femoral component of a knee joint prosthesis. Such a design is advantageous because it avoids the need to cement augmenting devices to the inferior surface of the femoral component. As a result, augmenting devices of varying thicknesses can be fitted into place on the inferior surface of the femoral component. The augmenting devices can be removed and replaced with devices having different dimensions until the proper augmentation thickness is determined. Such an augmentation system, however, requires a specially constructed femoral component.

Despite existing augmentation systems, there remains a need to provide improved systems that allow standard augmenting components to be easily and securely affixed within a prosthesis component. The cost of joint prostheses that utilize many current augmentation systems can be quite high because the tight tolerances required often result in a high scrap rate. There is thus a need for an augmentation system that allows augmenting devices to be easily and securely fitted to prosthesis components.

It is thus an object of the invention to provide a prosthesis augmentation system that securely and easily fits within a component of a joint prosthesis. A further object is to provide an augmentation system that offers more cost effective manufacturing potential as well as a reduced part rejection rate. Another object is to provide an augmentation system that is well suited for use with femoral components of knee joint prostheses. It is also an object to provide an augmentation system that offers a great deal of versatility in that it can be used with different types of femoral components, including cruciate retaining and cruciate sacrificing femoral components. A further object is to provide an augmentation system that can be used in a prosthesis component without the need for post-casting modification of the prosthesis. Yet another object is to provide an augmentation system that can be easily installed without compromising prosthesis alignment. Other objects will be apparent to those of ordinary skill in the art upon reading the description that follows.

SUMMARY OF THE INVENTION

The present invention relates to an augmentation system for use with joint prostheses. The system of the present invention serves to provide increased thickness to prosthesis components where boney deficiencies exist in the bones of a patient to which the prosthesis is to be secured. The augmentation system of the invention is particularly well suited for use in augmenting a femoral component of a knee prosthesis.

The augmentation system of the invention includes an augmenting block having first and second surfaces, which in one embodiment may correspond to distal and proximal surfaces, respectively. An aperture is formed in the augmenting block and extends between the first and second surfaces of the augmenting block. An expansion collet is secured within the aperture such that a stem at a distal end of the collet extends beyond the first surface of the augmenting block. An internal cavity is formed within at least a proximal portion of the collet and an expansion pin is adapted to seat within this cavity. The expansion pin cooperates with the collet such that advancement of the expansion pin within the collet facilitates the expansion of the outer diameter of the distal stem portion of the collet.

The expansion pin can be a threaded set screw or an elongate member having positive surface features, or simply an increasing diameter, which serves to expand the collet upon advancement of the pin.

In one embodiment cooperating ramped surface features are present on an internal surface of the collet cavity as well as on an external surface of the expansion pin. Moreover, the diameter of the expansion pin increases from a distal-most surface feature to a proximal-most surface feature. These ramped surfaces cooperate in the manner of a ratchet and pawl mechanism. The surface features are configured such that advancement of the expansion pin within the collet cavity causes the collet to expand and prevents the expansion pin from being moved in the reverse direction (i.e., withdrawn) once the surface features of the expansion pin and the collet cavity have engaged one another.

The augmenting block can be of a variety of shapes and dimensions suitable to be disposed at various desired locations within an implantable prosthesis, such as a femoral component of a knee joint prosthesis. For example, the augmenting block can be disposed on the inferior surfaces of an artificial knee joint femoral component, including on the posterior chamfer, the posterior flange of the condyle (medial or lateral side), or at the inferior surface of a condyle (lateral or medial side).

Preferably, the augmenting block is secured to a joint prosthesis component, in a desired location, by positioning the distal stem of the collet within a mounting cavity formed in the joint prosthesis. Once the augmenting block is properly positioned and aligned, the expansion pin is advanced within the collet thereby expanding the diameter of the distal stem of the collet to the extent that it engages the inner walls of the cavity. Complete advancement of the expansion pin causes expansion of the distal stem of the collet and results in secure placement of the augmenting block on the prosthesis such that the collet grabs the cavity of the prosthesis with a pulling axial load. Among the noteworthy advantages of this augmentation system are the reduced assembly time during surgical procedures and the tight securement of the augmenting block to the prosthesis. In one embodiment the expansion pin cannot be removed from the collet cavity once it has been advanced therein to a predetermined distance.

DETAILED DESCRIPTION OF THE INVENTION

As illustrated in FIGS. 1 through 5, the augmentation system 10 includes an augmenting block 12 having extending therethrough an aperture 14 which is substantially centrally located. Augmentation system 10 further includes an expandable collet 16 that is disposed within aperture 14 and an expansion pin 20 which is disposed within an internal cavity 17 at a proximal portion of the collet.

By way of example, the present augmentation system is described with reference to an anticipated use in augmenting a femoral component of a knee joint prosthesis. It is understood, however, that this augmentation system may be adapted for use in a variety of joint prostheses. A particular advantage of the present augmentation system, which lends itself to use with various types of joint prostheses, is the ease with which it is secured to a prosthesis. Moreover, this augmentation system is able to be firmly secured to a prosthesis, with little or no relative movement between the augmentation components and the prosthesis. The prosthesis further does not require post-casting machining processes to accept the augmentation system. One of ordinary skill in the art will be able to alter the shape and dimensions of the augmentation system described herein to fit other prostheses.

The augmentation block 12 illustrated in FIGS. 1 through 5 is adapted to mount on either the medial or lateral inferior condylar surfaces 44, 46 of a femoral component 34 of an artificial knee joint. Block 12 may be adapted for use in either left or right side knee prostheses. An augmenting block suitable for a left side prosthesis can mount upon either the medial or lateral inferior condylar surfaces 44, 46 thereof, and an augmenting block suitable for a right side prosthesis can mount upon either the medial or lateral inferior condylar surfaces of the prosthesis. As illustrated, block 12 has a first (distal) surface 22 and a second (proximal) surface 24. The area of the proximal surface 24 preferably is greater than the area of the distal surface 22 in order for the block to conform to the geometry of the inner condylar surface of a knee joint femoral component.

Figure 1:
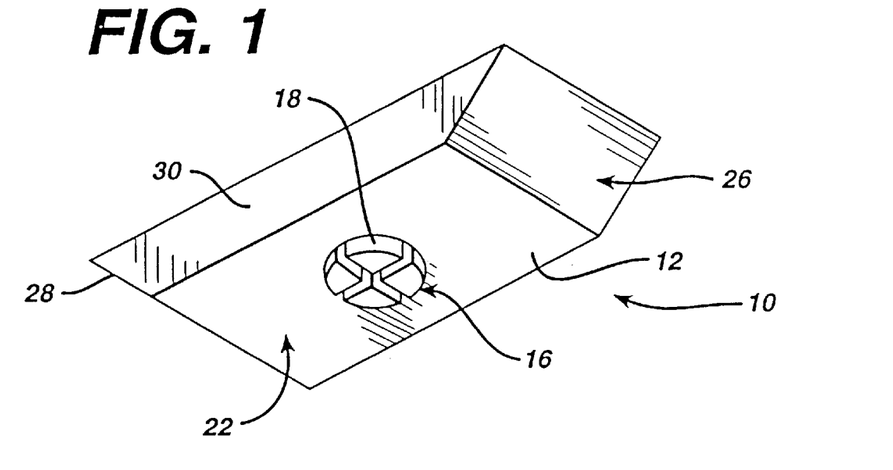
FIG. 1 is a perspective view of an augmentation system constructed according to the present invention.
Figure 2:
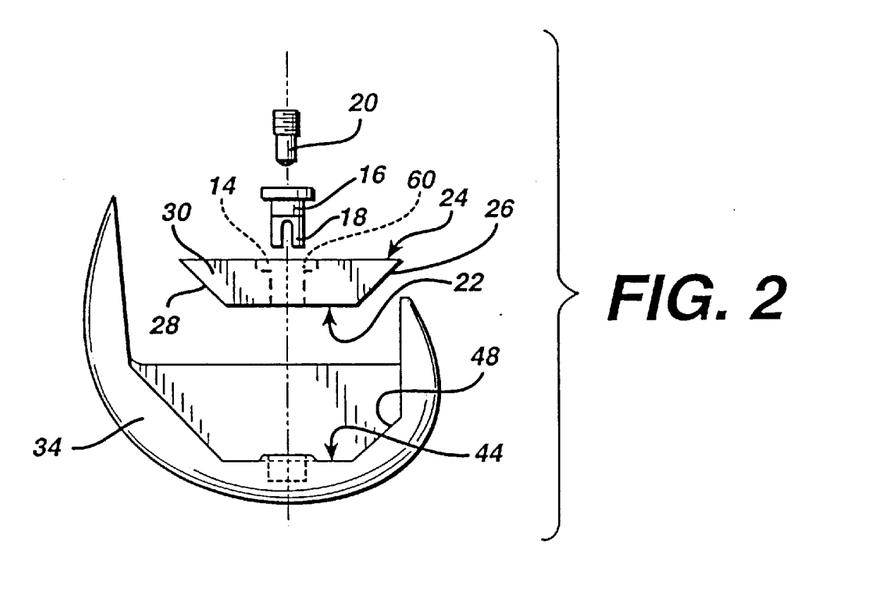
FIG. 2 is an exploded view of an augmentation system constructed according to the present invention, illustrating a femoral component of a knee prosthesis, an augmenting block, an expandable collet, and an expansion pin.
Figure 3:
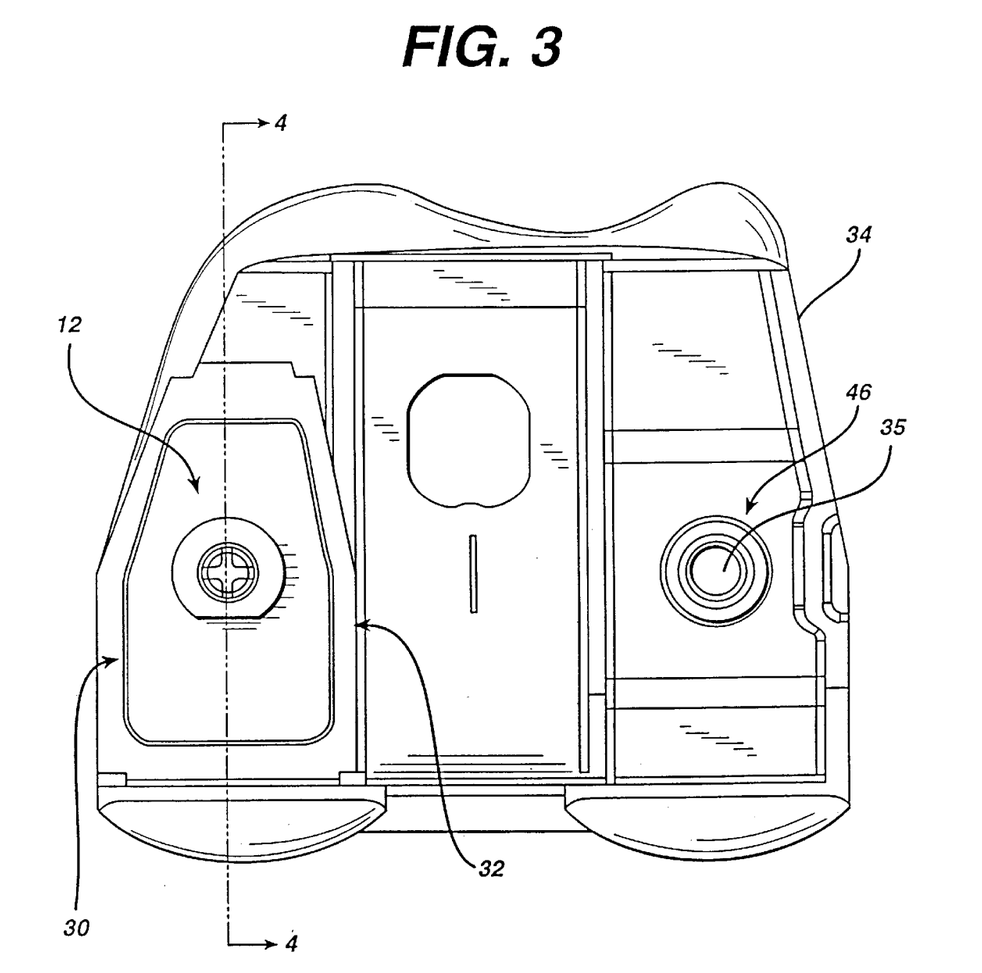
FIG. 3 is a top view of the augmentation system illustrated in FIG. 1, mounted within a knee femoral component.
Figure 4:
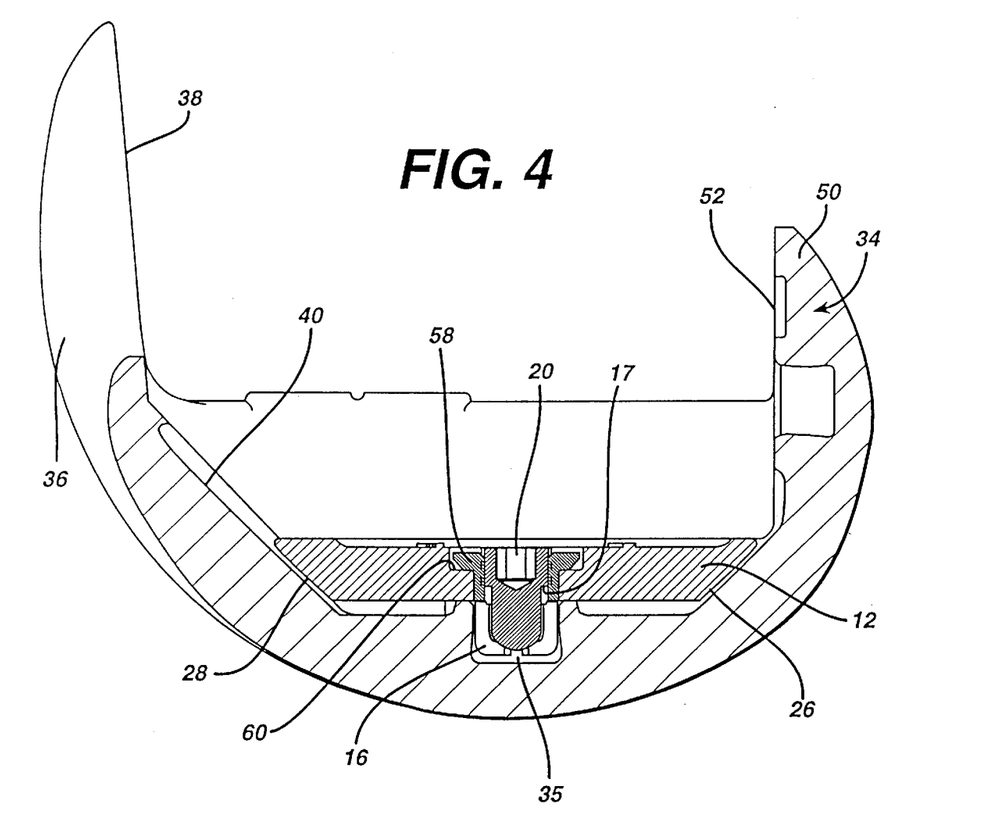
FIG. 4 is a sectional view, at lines 4—4, of an augmentation system of FIG. 3.
Figure 5:
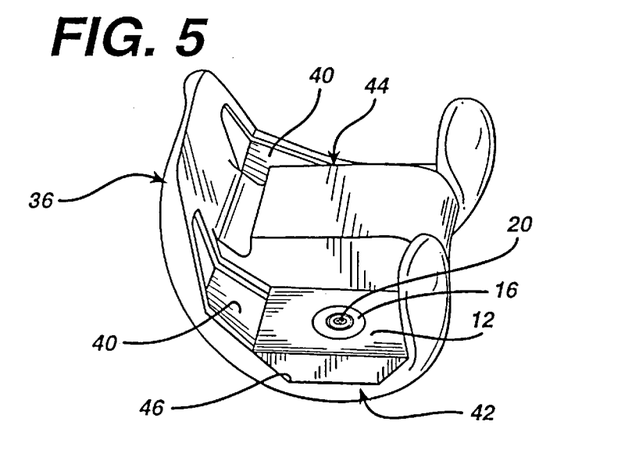
FIG. 5 is a perspective view of the augmentation system of the type shown in FIG. 1 disposed on the inferior surface of a medial condyle of the femoral component of a knee joint prosthesis.

Augmenting block 12 has two opposed, canted surfaces 26, 28 that can be either posterior or anterior surfaces, depending upon whether the augmentation block is mounted on the medial or lateral sides, or on a left or right side prosthesis. Preferably, surfaces 26, 28 are canted such that each surface slopes inwardly from the proximal surface 24 to the distal surface 22 as shown in FIG. 4. The angle of the canted surfaces 26, 28 can vary as will be appreciated by those having ordinary skill in the art. As shown in FIG. 5, the angle of surfaces 26, 28 corresponds to the angle of the anterior and posterior chamfers 40, 48 of a femoral component 34 to enable proper seating of the augmenting block 12 within a femoral component.

Augmenting block 12 further includes surfaces 30, 32 which correspond to either medial or lateral facing surfaces, depending upon whether the augmentation block 10 is used on the lateral or medial sides of a prosthesis, or in a left or right side prosthesis. Side surfaces 30, 32 preferably are substantially vertical and extend at a right angle with the plane of the proximal or distal surfaces 24, 22.

Figure 6A:
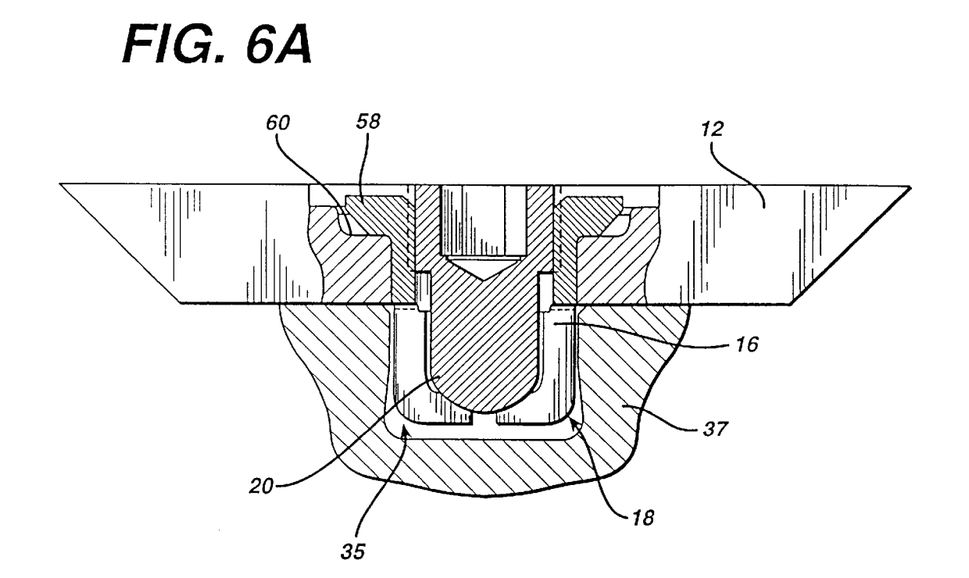
FIG. 6A is a partial sectional view showing engagement of the augmentation system of the invention with a prosthesis with the collet stem in a non-expanded condition.
Figure 6B:
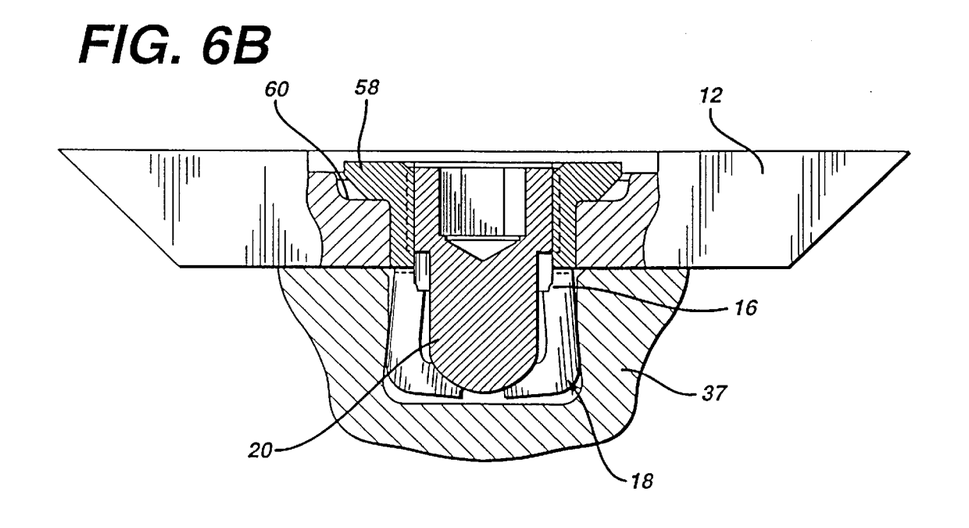
FIG. 6B is a partial sectional view illustrating the engagement of the augmentation system of the invention with the prosthesis with the collet stem in the expanded condition.

As illustrated in FIGS. 5, 6A and 6B, augmentation block 12 is adapted to mount on a prosthesis component, such as the inferior surface of the lateral or medial condyles 44, 46, such that the distal surface 22 of block 12 contacts the inferior surface of femoral component 34. The distal stem 18 of collet 16 preferably extends beyond the distal surface of block 12 by a distance sufficient to enable distal stem 18 of collet 16 to fit within a mounting cavity 35 disposed in a surface of the femoral component to be augmented. The frictional and/or mechanical engagement of the distal stem 18 of collet 16 enables the augmentation system 10 to be secured to an appropriate surface of the femoral component. The distance by which distal stem 18 extends beyond distal surface 22 of block 12 will vary depending upon the requirements of a given application. Typically, this distance is about 0.155 to 0.175 inch, and most preferably about 0.165 inch. The length of the distal stem 18 should not be so great that its distal end contacts the bottom of cavity 35.

As noted above, expansion pin 20 controls the expansion (and, optionally, the contraction) of the distal stem 18 of collet 16. In one embodiment, where the expansion pin is a threaded set screw, tightening the expansion pin expands the distal stem 18, while loosening pin 20 enables a once expanded distal stem 18 to contract. FIG. 6A illustrates the mounting of augmentation block 12 to a prosthesis component 37 while distal stem 18 of collet 16 is in a non-expanded condition. When stem 18 is in the non-expand condition, there is little or no frictional and/or mechanical engagement between stem 16 and mounting cavity 35; the augmentation block 12 can be freely removed and inserted into mounting cavity 35 in this condition. FIG. 6B illustrates the mounting of augmentation block 12 upon a prosthesis component 37 when the stem 18 is in the expanded condition. In this condition, sufficient frictional and/or mechanical engagement exists between the stem 18 and the walls of the mounting cavity 35 to enable the augmentation block to be held firmly on the prosthesis component.

Figure 10A:
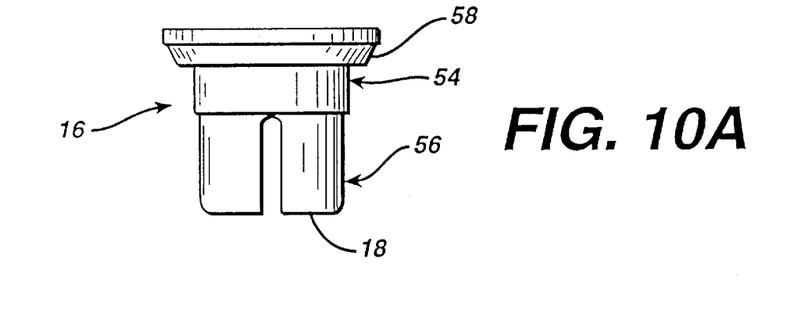
FIG. 10A is a side view of an expandable collet useful with the present invention.
Figure 10B:
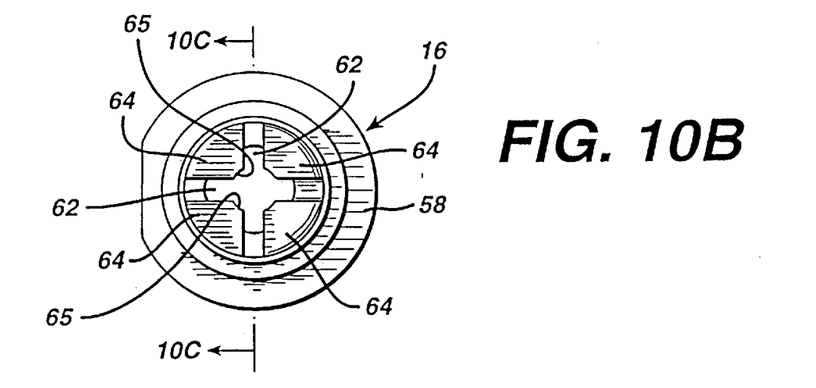
FIG. 10B is a bottom view of the collet shown in FIG. 10A.
Figure 10C:
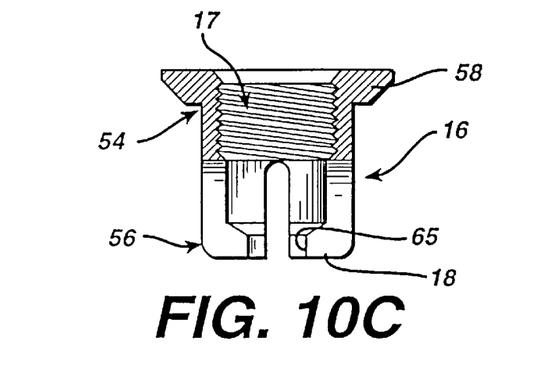
FIG. 10C is a cross-sectional view, at lines 10C—10C, of the collet shown in FIG. 10B.

Collet 16, as illustrated in FIGS. 10A, 10B, and 10C, includes a proximal region 54 and a distal region 56. Proximal region 54 includes a collar 58, which can mount within a recessed area 60 in the proximal surface of augmenting block 12, as shown in FIGS. 4, 6A and 6B. The collar 58 and recessed area 60 can be of virtually any corresponding shapes, including for example, circular and D-shaped. A D-shaped collar, or another irregularly shaped collar, can be useful to prevent any unwanted rotation of the collet within aperture 14.

The distal stem 18 of collet 16 preferably is slotted, with two perpendicular slots 62 extending therein. Preferably, the slots 62 separate the stem into four substantially triangular shaped wedges 64, when viewed from the bottom as shown in FIG. 10B. FIG. 10C illustrates that the interior portion of distal stem 18 is angled inwardly to the tip 65 of wedges 64. This configuration enables the internal geometry of the distal stem 18 to cooperate with a radius tip 66 at a distal end of screw 20, as shown in FIG. 11, to cause the distal stem 18 of collet 16 to expand and the wedges 64 to separate when distal end 74 of the pin 20 is forced into engagement with the corresponding internal surfaces of wedges 64.

Figure 13:
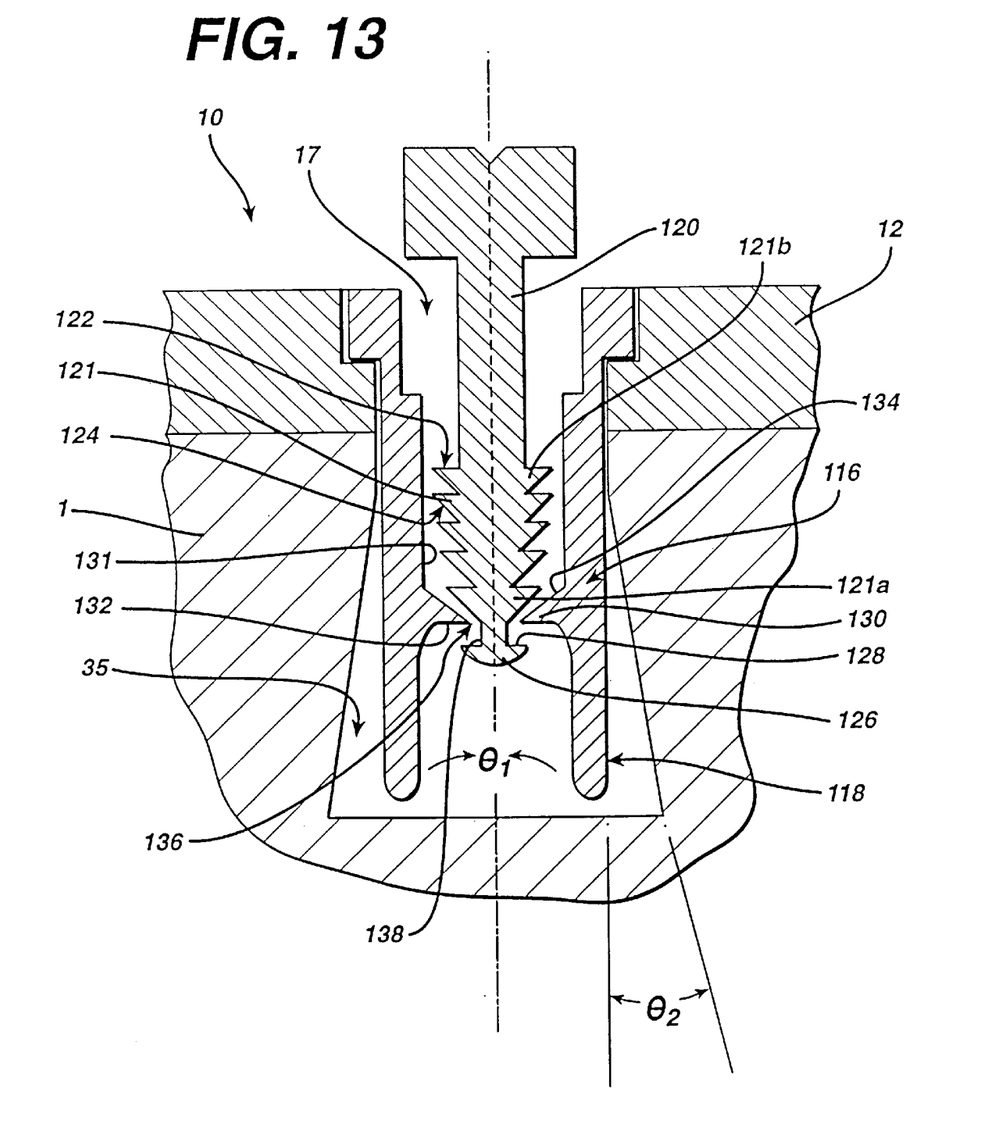
FIG. 13 is a side, sectional view of an alternative augmentation system illustrating the collet in the non-expanded condition.
Figure 14:
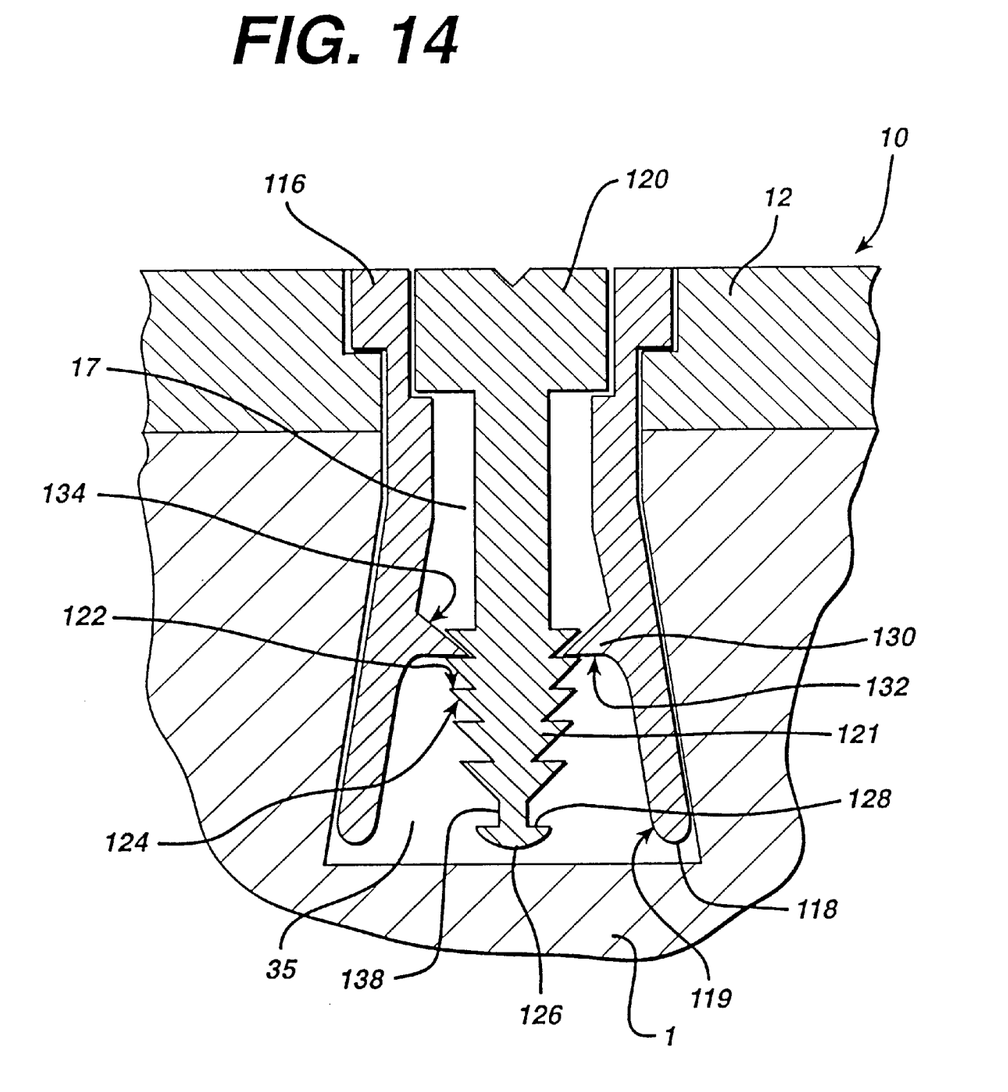
FIG. 14 is a side, sectional view of the augmentation system shown in FIG. 13 illustrating the collet in the expanded condition.

It is not necessary that the collet have two slots disposed therein to form four triangular wedges 64 or legs. It will be readily apparent to one having ordinary skill in the art that collet 16, 116 may have one or more slots disposed therein. FIGS. 13 and 14 illustrate an embodiment in which collet 116 has one slot disposed therein to form two expandable legs at distal end 118.

Figure 11:
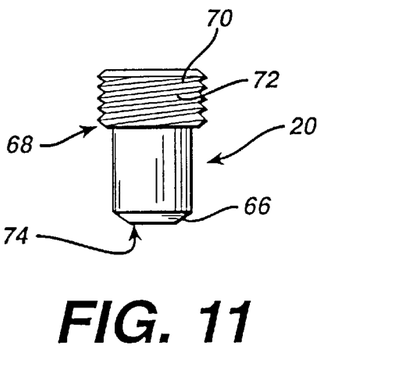
FIG. 11 is a side view of a threaded expansion pin useful with one embodiment of the augmentation system of the present invention.

As illustrated in FIG. 11, pin 20 also includes a proximal end 68 having a head portion 70. In one embodiment, as illustrated in FIG. 11, the head further includes a threaded region 72 that engages an internally threaded region of the collet 16. A distal end 74 of expansion pin 20 preferably has a geometry that will cause expansion of the distal stem of the collet. The distal end 74 of the pin can include a radius tip point 66, a dogged end (not shown), or similar geometries. Preferably, the head 70 of the screw-type expansion pin is a hex head.

The dimensions of the aperture 14 in the augmentation block 12, the collet 16, and the mounting cavity 35 of the femoral component can vary as will be understood by one of ordinary skill in the art. It is essential, however, that the relative dimensions of the components be such that the collet 16 have a relatively tight frictional fit within aperture 14, and that rotation of the collet within aperture 14 be prevented. In a preferred embodiment the collet 16 has a diameter slightly greater than the diameter of the aperture 14. Thus, the collet 16 is press fit within aperture 14 to prevent rotation and separation. Preferably the size differential ranges from about 0 to 0.002 inch.

Further, the non-expanded stem 18 should fit within the mounting cavity 35 without excessive friction. The expanded stem 18 should firmly engage the inner walls of mounting cavity 35 to prevent dislodgment or movement of the augmentation block 12. The dimensions of these components will vary depending upon the requirements of a given application, however one of ordinary skill in the art can readily determine the desired dimensions. Generally, the diameter of the distal stem 18 of the collet 16 in the non-expanded condition is approximately 0.240 to 0.260 inch, and preferably about 0.250 inch. The diameter of the distal stem 18 of collet 16 in the expanded condition preferably is about 0.010 to 0.020 inch greater than the diameter in the non-expanded condition. The diameter of the mounting cavity 35 is sufficient to yield a secure interference fit between the collet stem and the cavity when the collet stem is expanded. Preferably, the mounting cavity has a diameter of about 0.26 inch, ±0.10 inch. The depth of mounting cavity 35 can vary, as will be understood by those having ordinary skill in the art, but preferably the depth is about 0.18 to 0.206 inch. As noted above, the distal stem 18 of collet 16 should not bottom out within cavity 35.

The collet and expansion pin can also be of dimensions that are readily ascertainable to one of ordinary skill in the art. Preferably, the collet has a length of approximately 0.25 to 0.60 inch and the expansion pin has a length of approximately 0.16 to 0.18 inch. These dimensions obviously will vary depending upon the size and shape of the prosthesis to be augmented.

Figure 7:
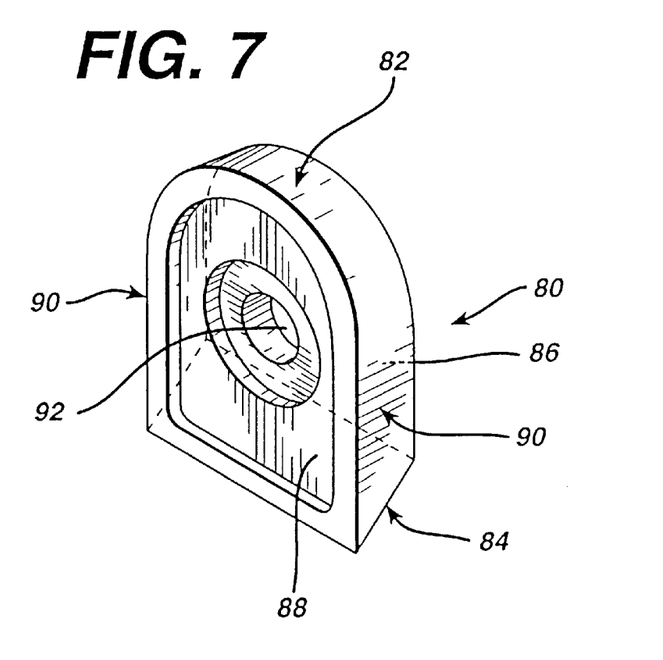
FIG. 7 is a perspective view of an augmentation system of the present invention adapted to fit a femoral component of a knee joint prosthesis at the inferior surface of the posterior flange thereof.
Figure 8:
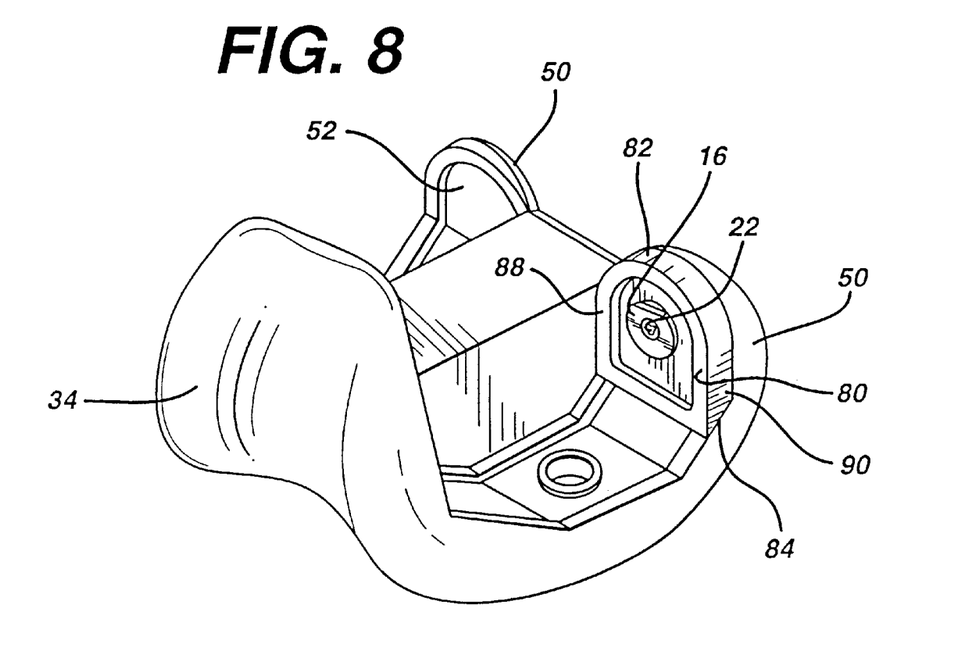
FIG. 8 is a perspective view illustrating the augmentation system of FIG. 7 mounted to a knee joint prosthesis.
Figure 9:
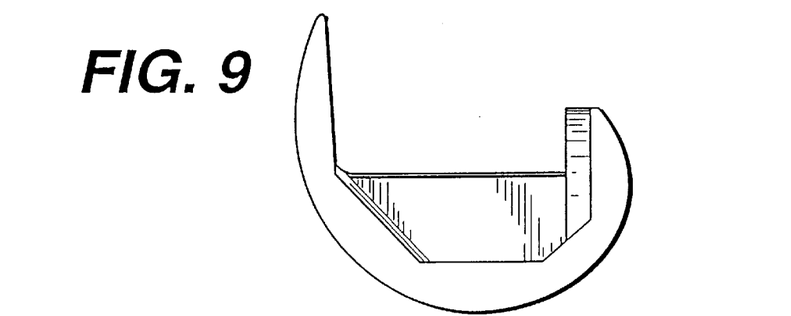
FIG. 9 is a side view of the augmentation system illustrated in FIG. 8.

FIGS. 7 through 9 illustrate one example of an alternative augmenting block 80 that is useful for augmenting another area of a knee femoral component. Augmenting block 80, is constructed to be suitable for mounting on the inferior surface 52 of either the lateral or medial posterior flanges 50. As illustrated, augmenting block 80 includes a convex or dome-like proximal surface 82 and a distal surface 84 that is canted in order to seat on the posterior chamfer 48 of femoral component 34. Anterior surface 86 of block 80 is non-canted and is adapted to mount against the inferior surface 52 of the lateral or medial posterior flange 50 of femoral component 34. Posterior surface 88 of block 80 is likewise non-canted and extends in a plane that is parallel to the plane of anterior surface 86. Lateral and medial sides 90 are also non-canted and are oriented perpendicularly to surfaces 86 and 88. Aperture 92 extends from the posterior surface 88 to the anterior surface 86 and is adapted to seat collet 16 in the manner described above with respect to FIGS. 1 through 6B. The distal stem 18 of the collet 16 extends beyond the anterior surface of block 80, and is adapted to seat within a mounting cavity 35 disposed in the inferior surface 52 of lateral or medial posterior flange 50.

Figure 12A:
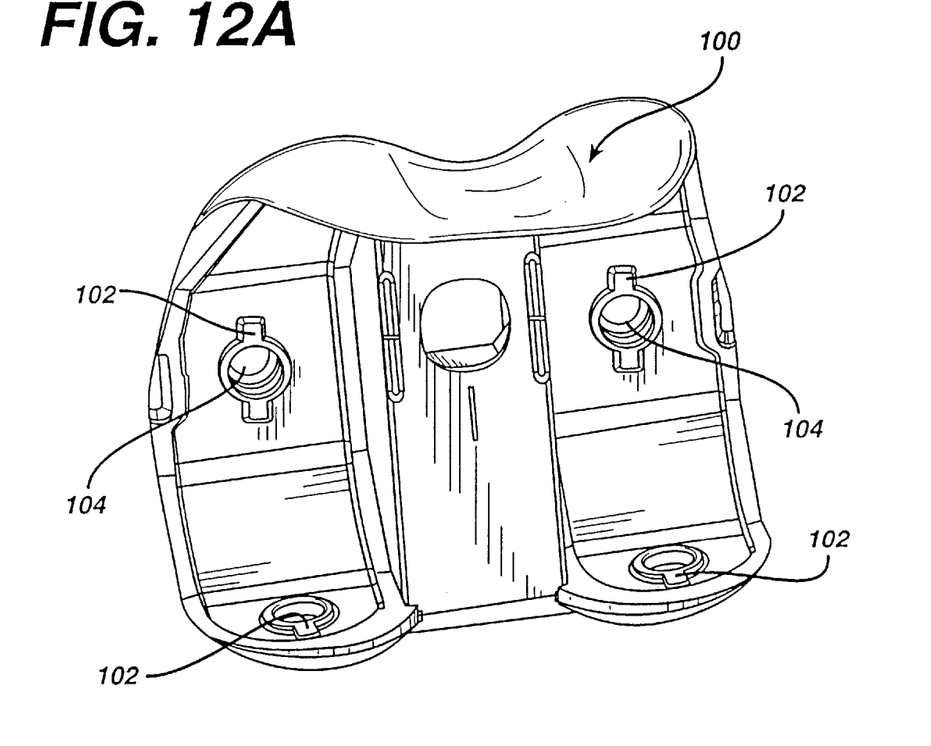
FIG. 12A is a top view (of the inferior surface) of a femoral component useful in connection with the present invention.
Figure 12B:
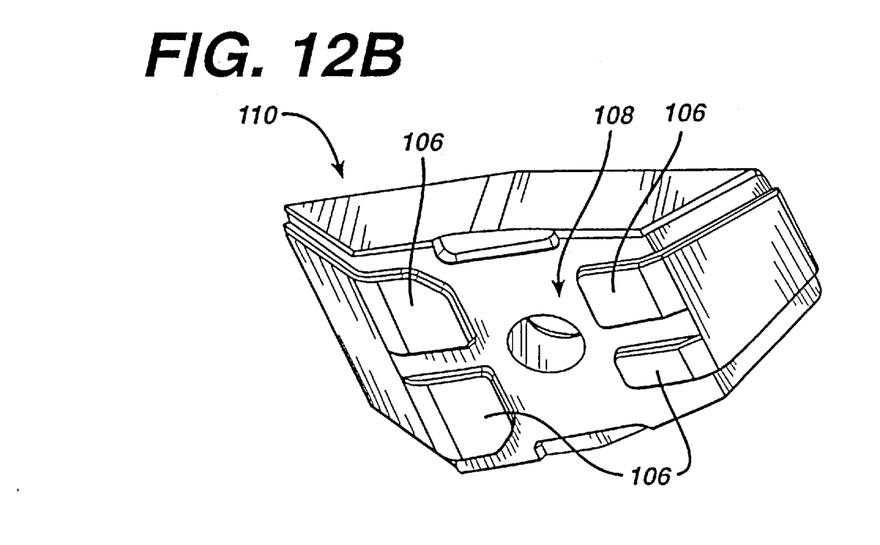
FIG. 12B is a perspective view, illustrating the distal surface, of an augmenting block according to the present invention.

As shown in FIGS. 12A and 12B, the augmentation system of the invention may be configured to include surface features that serve to prevent rotation of an augmenting block once it has been mounted upon a prosthesis. Knee femoral component 100 includes raised femoral surface features 102 surrounding and adjacent mounting cavities 104. The raised femoral surface features cooperate with raised surface features 106 an the distal surface 108 of augmenting block 110. Although these surface features are described only with respect to an augmenting block that mounts upon the inferior condylar surface of a knee femoral, it is understood that surface features may be used with augmenting systems that mount in other regions of a knee femoral, and with augmenting systems that mount in other prostheses. Further, one of ordinary skill in the art can easily vary the shape and dimensions of such surface features.

FIGS. 13 and 14 illustrate an alternative embodiment of the invention which utilizes a non-threaded expansion pin 120. In this embodiment expansion pin 120 is similar in construction to expansion pin 20, described above, except that it includes raised, ratchet-like positive surface features 121 at a distal portion thereof. Preferably, each surface feature 121 is of a substantially triangular cross section having a substantially horizontal proximal-facing surface 122 and a canted distal-facing surface 124. A distal end of pin 20 includes a dogged distal tip 126 which includes a substantially horizontal shoulder 128.

One of ordinary skill in the art can readily determine suitable dimensions of the expansion pin as well as the dimensions for other elements of the augmentation system of the invention. By way of example, however, the outer diameter of the expansion pin 120, in a region thereof that includes surface features 121, increases from the distal-most surface feature 121a to a proximal-most surface feature 121b. The outer diameter of the pin 120 in this region preferably ranges from about 1/8 to 1 inch at surface feature 121a to about 3/16 to 1 1/16 inches at surface feature 121b. The slope of this increasing diameter is defined by an angle $\theta_1$, which can also be determined by one of ordinary skill in the art. Preferably, the angle $\theta_1$ is in the range of about 0.5 to 20°.

The height of each surface feature 121, as measured from base to apex, can vary depending upon the requirements of a given application. Preferably this height is in the range of 1/64 to 1/4 inch. The increasing diameter of the pin 120 can be achieved by increasing the height of more proximally disposed surface features, relative to the height of distal surface features. Alternatively, increased diameter can be achieved by maintaining surface features at a substantially constant height while increasing the nominal inside diameter of the pin 120 in the region in which surface features are present. The inside diameter of the expansion pin 120 is understood to refer to the diameter of the expansion pin measured from base to base of surface features 121.

Mounting cavity 35, as illustrated in FIGS. 13 and 14, preferably is constructed such that its diameter increases from an intermediate depth of the cavity to the bottom (or distal end) of the cavity. Preferably, the angle $\theta_2$ defined by the reverse taper of mounting cavity 35 is in the range of about 0.5 to 20°. In a preferred embodiment the angles $\theta_1$ and $\theta_2$ are substantially equal.

The angle at which canted distal facing surface 124 is disposed can vary. However, this surface is preferably canted at an angle of about 20 to 70° as measured from horizontal. One of ordinary skill in the art will appreciate that the surface may be canted at an angle outside of this range.

Collet 116 is similar in construction to collet 16, described above, except that the collet 116 includes a pawl-like surface feature 130 disposed on interior wall 131 thereof. Like collet 16, collet 116 is slotted at its distal end to form two or more legs 119. Surface feature 130, which is substantially triangular in cross section, includes a substantially horizontal distal-facing surface 132 and a canted proximal-facing surface 134.

Preferably, a single surface feature 130 is present on interior wall 131 of collet 116. The height of surface feature 130, as measured from base to apex, should be sufficient to cause all surface features 121 and dogged distal tip 126 to pass past the surface feature with mechanical interference. Preferably, the height of surface feature 130 is in the range of about 1/64 to 1/4 inch.

Surface feature 130 includes a substantially horizontal distal facing surface 132 and a canted proximal facing surface 134. The angle at which surface 134 is disposed should be substantially the same as the angle at which the canted surface 124 of surface feature 121 is disposed. Thus, the angle of surface 134 preferably is in the range of about 20 to 70° as measured from horizontal.

FIG. 13 illustrates that expansion pin 120 is disposed within collet 116 at an initial position. At this initial position the mechanical engagement of the pin 120 and the collet 116 results in little or no expansion of the collet 116. Thus, insufficient frictional force is exerted by the distal stem 118 of collet 116 against the walls of mounting cavity 35 to enable the augmentation system 10 to be secured to prosthesis 1.

However, when the pin 120 is at the initial position, the pin 120 is disposed within the collet such that it cannot be removed. Once distal tip 126 of pin 120 passes beyond surface features 130 of collet 116 the pin cannot be removed from the collet. The dogged tip 126 of pin 120 is curved so as to enable it to fit through the space 136 defined by surface features 130. As tip 126 passes the surface feature 130 the collet 116 is momentarily expanded. The collet returns to its non-expanded condition once neck region 138 is positioned adjacent surface feature 130. Once tip 126 passes through space 136 the horizontal surface 132 of surface feature 130 and horizontal surface 128 of dogged tip 126 abut one another, thereby preventing enough expansion of the collet to remove the pin 120.

An important feature of the expansion pin of the invention is that it be of a design and construction that is suitable to expand the collet. Thus, alternatives to the expansion pin constructions described above may also serve this purpose. For example, the expansion pin can also be in the form of a dowel, either smooth or toothed, having a diameter which increases from a distal end to a proximal end thereof.

FIG. 14 illustrates that the action of pressing pin 120 into cavity 17 within collet 116 causes expansion of legs 119 of collet 116 to an extent that they engage the interior walls of cavity 35 with sufficient force to secure the augmenting block 12 to prosthesis 1. Once pin 120 is advanced within collet 116 the increasing diameter of pin causes the legs 119 of the collet to separate thereby expanding the distal stem 18 of the collet.

The expansion pin 120 can be inserted within collet 116 by any tool that is capable of applying an axial load to the pin. A variety of clamping tools, well known to those having ordinary skill in the art, can thus be used to accomplish this insertion. One example of such a clamping tool is a hand-held punching device to which pressure is applied to advance pin 120. Preferably, a suitable tool would cradle or support the main components of the augmentation device while guiding a punch element, which advances the pin, to maintain coaxiality of the force. It is also possible to use a two-jaw clamping device, similar to a patellar clamp, one jaw of which cradles the main component while the other jaw advances the pin 120.

An advantage presented by the embodiment illustrated in FIGS. 13 and 14 is that the force used to advance pin 120 within collet 116 is an axially directed force. Thus, there is little or no possibility that torque will develop and result in displacement or misalignment of the augmenting block. Further, the engagement of surfaces features 121 of pin 120 with surface feature 130 of collet 116 is such that the pin cannot be removed from the collet once it is disposed at an initial position within the collet. As discussed above, the engagement of horizontally oriented surfaces on the surface features of the pin and the collet prevented the removal of the pin.

The dimensions of the augmentation system of the invention can vary as required by the dimensions of the joint prosthesis with which the system is to be used and the amount of augmentation that is required. One of ordinary skill in the art will be able to determine the proper dimensions of the augmentation system 10 of the present invention so as to closely fit the configuration of the inferior surfaces of a joint prosthesis (such as a femoral component) with which the augmentation system is to be used. Generally, the thickness (proximal to distal for augmenting block 12, anterior to posterior for augmenting block 80) of the augmentation system is in the range of about 2 to 20 mm while the width of the augmentation system (medial to lateral) ranges from about 10 mm to 40 mm, and the length (anterior to posterior for augmenting block 12, or proximal to distal for augmenting block 80) ranges from about 10 mm to 60 mm.

The augmentation system of the invention can be made from a variety of biocompatible materials having high strength, durability and resistance to wear debris. Examples of such materials include metal alloys such as cobalt chromium alloy, titanium alloy, stainless steel, ceramics and other materials, including polymers, that are well known for use in the manufacture of implantable bone prostheses.

A preferred material for the augmentation system, as well as for many prostheses, is a cobalt chromium alloy such as ASTM F-75.

The collet components preferably are made from a malleable metal or metal alloy to reduce the risk of tensile failure as a result of collet expansion. Where such materials are used to form a threaded component, the materials should be able to deform (but not fail) when subjected to a torque of about 20 to 65 in lbs, and more preferably about 25–35 in-lbs. A preferred material is a wrought cobalt chromium alloy such as ASTM F-90.

The expansion pin preferably is made from a metal or metal alloy that has a higher modulus and a greater hardness than does the collet. Such properties ensure that the collet will deform (and not the expansion pin) when subjected to torque and/or axial load. A preferred material from which the expansion pin can be manufactured is wrought cobalt chromium alloy such as ASTM F-1537 (formerly known as ASTM F-799).

The augmentation system of the invention offers many advantages. For example, the augmentation system is able to be secured to a joint prosthesis (such as a knee femoral component) without bone cement, in a secure fit, with improved tensile securement values, such that relative motion between the joint prosthesis and the augmentation system is relatively low or nonexistent. The tensile securement values preferably are in the range of about 50 to 500 kg. This secure fit ensures that the performance of the augmented prosthesis component is not compromised. Moreover, the augmentation system of the invention can be easily attached within a femoral component of a knee joint prosthesis. Of particular significance is the fact that the augmentation system of the invention can be used in both left and right side joint prostheses, and in various areas of joint prostheses without modification. The augmentation system of this invention also offers the advantage that the collet can secure the augmenting block to a prosthesis by securely engaging a mounting cavity within the prosthesis having an as cast tolerance.

The foregoing description of the illustrative embodiment of the invention is presented to indicate the range of constructions to which the invention applies. Variations in the physical architecture and dimensions of the augmentation system will be apparent to those having ordinary skill in the art based upon the disclosure herein, and such variations are considered to be within the scope of the invention in which patent rights are asserted, as set forth in the claims appended hereto. All publications and references cited herein are expressly incorporated herein by reference in their entirety.

What is claimed is:

1. An augmentation system for a joint prosthesis comprising an augmenting block, mountable on a joint prosthesis, the augmenting block having first and second opposed surfaces;

an aperture formed in the block and extending between the first and second surfaces thereof;

an expansion collet disposed within the aperture such that a stem at a distal end thereof extends beyond the first surface of the augmenting block, the expansion collet having a slotted distal end and an internal cavity formed within the collet;

at least one raised feature formed on the internal surface of the cavity of the collet; and a set pin element, disposable within the internal cavity of the expansion collet, for expanding the diameter of the collet, the set pin having a plurality of raised features formed on the outer surface thereof such that the diameter of the pin element increases in the direction from the distal-most feature to the proximal-most feature.

2. The system of claim 1 wherein the surface feature within the collet is of a substantially triangular cross section.

3. The system of claim 2 wherein the surface feature within the collet has a distal-facing surface that is substantially horizontal and a proximal-facing surface that is canted.

4. The system of claim 3 wherein the proximal-facing surface feature within the collet is canted at an angle of about 20° to 70°, as measured from horizontal.

5. The system of claim 3 wherein the surface features on the set pin element are substantially triangular in cross section.

6. The system of claim 5 wherein the features disposed on the pin element have a distal-facing surface that is sloped and a proximal-facing surface that is substantially horizontal.

7. The system of claim 6 wherein the distal-facing surface of the features disposed on the pin element are canted at an angle of about 20° to 70°, as measured from horizontal.

8. The system of claim 1 wherein the prothesis includes a mounting cavity which is reverse tapered such that a diameter increases from an intermediate depth of the mounting cavity to a distal end of the cavity.

9. The system of claim 8 wherein the aperture has a reverse taper angle of about 0.5° to 20°, as measured from vertical.

10. The system of claim 9 wherein the diameter of the pin element increases at an angle, as measured from vertical, that is substantially equal to the reverse taper angle of the aperture.

11. The system of claim 1 wherein the collet is frictionally and/or mechanically engaged within the aperture.

12. The system of claim 11 wherein a recessed area of the first or second surfaces of the block surrounds the aperture of the augmenting block.

13. The system of claim 12 wherein the proximal end of the collet includes a collar that seats within the recessed area of the augmenting block.

14. The system of claim 13 wherein the collar is D-shaped.

15. The system of claim 13 wherein the collar is round.

16. The system of claim 1 wherein the distal end of the collet has a diameter ranging from about 0.240 to 0.260 inch in the non-expanded condition to about 0.250 to 0.270 inch in the expanded condition.

17. The system of claim 1 wherein the stem at a distal end of the collet is adapted to seat within a mounting cavity formed in a surface of a joint prosthesis.

18. An augmentation system for a femoral component of an artificial knee prosthesis, comprising a femoral component having an articulation surface and an opposed, bone engaging surface, the bone engaging surface having at least one mounting cavity defined by a wall disposed in a portion thereof;

an augmenting block, mountable on a portion of the bone engaging surface of the femoral component, the augmenting block having an aperture extending from first to second surfaces of the block;

an expansion collet disposed within the aperture of the augmenting block such that a stem at a distal end of the expansion collet extends beyond a first surface of the augmenting block, the expansion collet having an internal cavity formed therein, and a slotted distal end that is adjustable between a contracted condition in which the stem non-engagingly fits within the mounting cavity of the femoral component and an expanded condition in which the stem engages the wall of the mounting cavity to secure the augmenting block to the femoral component;

an internal cavity extending at least partially into the expansion collet;

at least one raised feature formed on an internal surface of the internal cavity of the collet; and a set pin element, disposable within the collet cavity, for expanding the diameter of the collet, the set pin having a plurality of raised features formed on the outer surface thereof such that the diameter of the pin element increases in the direction from the distal-most feature to the proximal-most feature.

19. The system of claim 18 wherein the surface feature within the collet is of a substantially triangular cross section.

20. The system of claim 19 wherein the surface feature within the collet has a distal-facing surface that is substantially horizontal and a proximal-facing surface that is canted.

21. The system of claim 19 wherein the proximal-facing surface feature within the collet is canted at an angle of about 20° to 70°, as measured from horizontal.

22. The system of claim 19 wherein the surface features on the set pin element are substantially triangular in cross section.

23. The system of claim 22 wherein the features disposed on the pin element have a distal-facing surface is canted and a proximal-facing surface that is substantially horizontal.

24. The system of claim 23 wherein the distal-facing surface of the features disposed on the pin element are canted at an angle of about 20° to 70°, as measured from horizontal.

25. The system of claim 18 wherein the diameter of the mounting cavity is reverse tapered such that the diameter increases from an intermediate depth of the mounting cavity to a distal end of the cavity.

26. The system of claim 25 wherein mounting cavity has a reverse taper angle of 0.5° to 20° as measured from vertical.

27. The system of claim 26 wherein the diameter of the pin element increases at an angle, as measured from vertical, that is substantially equal to the reverse taper angle of the mounting cavity.

28. The system of claim 18 wherein the collet is frictionally and/or mechanically engaged within the mounting cavity.

29. The system of claim 28 wherein a recessed area of a second surface of the block surrounds the aperture of the augmenting block.

30. The system of claim 29 wherein the proximal end of the collet includes a collar that seats within the recessed area of the augmenting block.

31. The system of claim 30 wherein the collar is D-shaped.

32. The system of claim 30 wherein the collar is round.

33. The system of claim 18 wherein the distal end of the collet has a diameter ranging from about 0.240 to 0.260 inch in the non-expanded condition to about 0.250 to 0.270 inch in the expanded condition.

* * * * *